United States Patent [19]

Varaprath et al.

[11] Patent Number: 4,861,906
[45] Date of Patent: Aug. 29, 1989

[54] PROCESS FOR THE SYNTHESIS OF ACYLAMINO ORGANOSILICON COMPOUNDS

[75] Inventors: Sudarsanan Varaprath; Padmakumari J. Varaprath, both of Midland, Mich.

[73] Assignee: Dow Corning Corporation, Midland, Mich.

[21] Appl. No.: 335,919

[22] Filed: Apr. 10, 1989

[51] Int. Cl.$^4$ ............................................. C07F 7/10
[52] U.S. Cl. ................................................. 556/419
[58] Field of Search ........................................ 556/419

[56] References Cited

U.S. PATENT DOCUMENTS

| | | | |
|---|---|---|---|
| 2,929,829 | 3/1960 | Morehouse | 556/419 |
| 4,507,455 | 3/1985 | Tangvey et al. | 556/419 X |
| 4,608,270 | 8/1986 | Varaprath et al. | 556/419 X |
| 4,788,310 | 11/1988 | Stein et al. | 556/419 |

Primary Examiner—Paul F. Shaver
Attorney, Agent, or Firm—Killworth, Gottman, Hagan & Schaeff

[57] ABSTRACT

Organosilicon compounds containing at least one acylamino-substituted hydrocarbon radical are prepared by reacting an organosilicon compound containing at least one amino-substituted hydrocarbon radical with an acyl halide in a nonaqueous solvent and in the presence of a metal alkoxide in a nonaqueous cosolvent.

20 Claims, No Drawings

PROCESS FOR THE SYNTHESIS OF ACYLAMINO ORGANOSILICON COMPOUNDS

BACKGROUND OF THE INVENTION

This invention relates generally to a method for preparing organosilicon compounds that contain silicon-bonded acylamino-substituted hydrocarbon radicals. More specifically, the method involves the reaction of aminoalkylsilanes and siloxanes with acyl halides in nonaqueous media and in the presence of metal alkoxides to produce acylamino organosilicon compounds.

Organosilicon compounds that contain silicon-bonded acylamino-substituted hydrocarbon radicals are well known and have been described in U.S. Pat. No. 4,608,270 to Varaprath which is herein incorporated by reference.

As mentioned in Varaprath U.S. Pat. No. 4,608,270 and as taught in U.S. Pat. No. 2,929,829 to Morehouse, Japan No. 51/08022 to Furuya et al, Japan No. 56/74113 to Takamizawa and West German No. DE 2365272 to Koetzsch et al., acylaminoorganopolysiloxanes can be synthesized by reacting aminosiloxanes with the corresponding acid chloride in the presence of a tertiary amine such as triethylamine. However, such a synthesis has several disadvantages. First, the removal of the voluminous precipitate of triethylamine hydrochloride by filtration is tedious. Second, a small amount of HCl is liberated even when an excess of amine is used. This HCl is detrimental to the stability of the polymer especially when the acid chloride has other reactive vinyl functionality such as where the acid chloride is acrylyl chloride.

An alternative method for the preparation for the acylamino organosilicon compounds involves the reaction of aminosiloxanes and silanes with an acid anhydride or ester at elevated temperature. This is taught in U.S. Pat. No. 4,507,455 to Tangney and Ziemelis, assigned to the assignee of the present invention. Unfortunately at the elevated temperatures of the reaction, arcylamide derivatives undergo Michael addition and amidation of the acrylic double bond resulting in unwanted byproducts and crosslinkage of the desired product which ultimately causes the polymer to gel.

Finally as taught in the above mentioned U.S. Pat. No. 4,608,270 to Varaprath, also assigned to the assignee of the present invention, these problems can be overcome by reacting the aminosilanes and siloxanes with acid chlorides in the presence of aqueous sodium hydroxide. However, a problem arises from the fact that this reaction is carried out in a two-phase system in which the aminosiloxane is dissolved in an organic solvent that is immiscible with water. The HCl that is produced on addition of acyl chloride is neutralized by hydroxide in the aqueous phase. Because the amide function is generally highly polar and hydrophilic, it shows a great tendency to absorb moisture. Incorporation of these units into the siloxane backbone increases water miscibility causing the polymers to emulsify easily thus making phase separation difficult. To some extent, this problem can be overcome by using chlorinated solvents such as methylene chloride or chloroform but, unfortunately, such solvents are toxic. Moreover, when larger amounts of amide functionality or more resinous structure or both are used, it becomes very difficult to prepare such compounds using a two-phase system even when chlorinated solvents are used. Finally, because of the presence of the aqueous phase, it is impossible to prepare aminosilanes containing hydrolytically unstable groups using this process.

Accordingly, the need remains for an improved method for preparing acylamino organosilicon compounds which avoids the phase separation and toxicity problems previously encountered. The need also remains for an expanded method which permits use of silane starting materials having hydrolytically unstable groups such as $CH_3\,OSi$.

BRIEF SUMMARY OF THE INVENTION

These needs are met by the present invention which is directed to a method for preparing organosilicon compounds that contain at least one silicon-bonded acylamino-substituted hydrocarbon radical using a nonaqueous solvent system. Preferably, an aminoalkylsilane or siloxane, that is, an aminosilicon compound having at least one silicon-bonded, amino-substituted hydrocarbon radical containing at least one nitrogen-bonded hydrogen, is reacted with an acyl halide in a nonaqueous and non-toxic solvent such as toluene or hexane. The silicon-bonded, amino-substituted hydrocarbon radical preferably has the formula $-Q(NHQ')_a\,NZH$ wherein Q and Q' are divalent hydrocarbon radicals, Z is H or a monovalent hydrocarbon radical, and "a" is 0 or 1. The acyl halide preferably has the formula $R''COX$ where $R''$ is a substituted or unsubstituted monovalent hydrocarbon radical and X is a halogen atom.

An alkali metal alkoxide such as sodium methoxide which may be in the form of a dry powder dissolved in a small amount of a cosolvent such as methanol, is used to neutralize the HCl that is produced in the primary reaction. Preferably the reaction is carried out at a temperature of from $-10$ to $10°$ C.

The use of nonaqueous solvents allows the use of organosilicon compounds with hydrolytically unstable functional groups such as the methoxy group. Likewise, because no separate aqueous phase is present, there are no phase separation problems.

Thus an improved process without many of the drawbacks of the prior art is provided for producing acylamino organosilicon compounds. As described in Varaprath U.S. Pat. No. 4,608,270, the acylamino organosilicon products are useful for paper release coatings and coupling agents. They are also useful as conformal coatings, for example, as moisture and radiation dual cure coatings of the type disclosed in copending applications Ser. Nos. 118,086, filed Nov. 6, 1986 and 200,827, filed June 1, 1988. Accordingly, it is an object of the present invention to provide an improved method for preparing organosilicon compounds that contain silicon-bonded acylamino-substituted hydrocarbon radicals of the type described in Varaprath U.S. Pat. No. 4,608,270. These and other objects of and advantages of the invention will become apparent from the following description and the appended claims.

DETAILED DESCRIPTION OF THE PREFERRED EMBODIMENTS

The preferred method consists of reacting an acyl halide with an aminosilicon compound having at least one silicon-bonded acylamino-substituted hydrocarbon radical containing at least one nitrogen-bonded hydrogen. The remaining silicon bonds are satisfied with organic radicals or divalent, silicon-linking, oxygen atoms, or both. The improved reaction of the present invention is carried out in the presence of a nonaqueous solvent, a metal alkoxide, and a small amount of cosolvent for the e metal alkoxide.

Typically the aminosilicon compound, a solvent, a metal alkoxide, and a small amount of cosolvent are mixed together. An acyl halide is dissolved in a solvent and gradually added to the mixture. After the addition is complete, the resulting mixture is agitated until the reaction is complete. The by-product metal halide is removed by filtration and the solvent can be removed if desired. The acyl halide can have any structure such as a linear, branched, or cyclic structure having aromatic, heterocyclic, olefinic or paraffinic bonding and containing one or more carbon-bonded —COX radicals, where X denotes a halogen atom. Preferably the acyl halide has the structure R″COX where X denotes a halogen atom such as I, Cl, Br, or F, preferably chlorine, and R″ denotes an unsubstituted or substituted monovalent hydrocarbon radical.

Examples of monovalent hydrocarbon radicals, i.e. R radicals, include, but are not limited to, alkyl radicals such as methyl, ethyl, propyl, butyl, hexyl, and octyl; cycloaliphatic radicals such as cyclohexyl; aryl radicals such as phenyl, benzyl, styryl, tolyl, xylyl, and biphenyl (xenyl); and alkenyl radicals such as vinyl and allyl. Examples of corresponding acyl halides include acetyl chloride, benzoyl chloride and, most preferably, acrylyl chloride, methacrylyl chloride, and cinnamoyl chloride.

Examples of substituted R radicals include, but are not limited to, halogenated radicals such as —CF$_3$ and —C$_6$H$_4$Cl, and other substituted radicals which are stable under the reaction conditions employed in the method of this invention such as —CH$_2$CH$_2$CN, —C$_6$H$_4$NO$_2$ and —C(CN)=CH$_2$.

The aminosilicon compound that is to be acylated can have any structure as long as it contains at least one silicon atom bonded to an amino-substituted hydrocarbon radical that bears one or more amino radicals at least one of which has a nitrogen-bonded hydrogen atom. The other silicon bonds are satisfied by organic radicals other than amino-substituted hydrocarbon radicals noted above or by divalent, silicon-linking oxygen atoms. Thus the aminosilicon compound can be a silane, a siloxane, a silcarbane, or a silcarbanesiloxane.

The silicon-bonded amino-substituted hydrocarbon radical has the formula —Q(NHQ′)$_a$NHZ where Q and Q′ denote divalent hydrocarbon radicals, Z denotes a hydrogen atom or a monovalent hydrocarbon radical, i.e., an R radical as defined previously , and "a" has a value of 0 or 1.

Examples of Q radicals and Q′ radicals include, but are not limited to, alkylene radicals such as ethylene, propylene, isopropylene, butylene, isobutylene, hexylene, octylene and arylene radicals such as phenylene, xylylene, etc. Q is preferably ethylene and Q′ is preferably propylene or isobutylene.

Examples of amino-substituted hydrocarbon radicals include, but are not limited to, NH$_2$CH$_2$CH$_2$CH$_2$—, CH$_3$NHCH$_2$CH$_2$CH$_2$—, NH$_2$CH$_2$CH(CH$_3$)CH$_2$—, NH$_2$CH$_2$CH$_2$NHCH$_2$CH$_2$CH$_2$—, NH$_2$CH$_2$CH$_2$NHCH$_2$CH(CH$_3$)CH$_2$—, NH$_2$(CH$_2$)$_6$NH(CH$_2$)$_3$—, and NH$_2$(CH$_2$)$_6$NHCH$_2$CH(CH$_3$)$_{CH2}$—. Silicon-bonded radicals, other than the above-noted amino-substituted hydrocarbon radicals, include organic radicals and divalent, silicon linking oxygen atoms. Examples of said organic radicals include, but are not limited to, divalent, silicon-linking hydrocarbon radicals such as the Q and Q′ radicals noted above, and halogenated derivatives thereof, alkoxy radicals such as methoxy radicals, hydroxy radicals, acyloxy radicals and hydrogen atoms. Preferably said organic radicals contain no more than 6 carbon atoms, such as methyl, 3,3,3 trifluoropropyl, phenyl and vinyl radicals, and most preferably are methyl or methoxy radicals.

The aminosilicon compounds to be acylated by the process of this invention are preferably silanes or siloxanes having the average formula R′$_c$ (NH$_2$(Q′NH)$_a$Q)$_d$SiO$_{(4−c−d)/2}$ where R′ denotes a monovalent hydrocarbon radical or an alkoxy radical as defined previously, where "a" is 0 or 1, "c" denotes a number having a value of from 0 to 3, such as 0, 0.5, 1.01, 2, 2.1, and 3, "d" denotes a number having a value of from >0 to 4, such as 0.01, 0.5, 1, 2, and 3, and "c" +"d" has a value of from 1 to 4 such as 1.5, 1.99, 2.01, 3, and 4. Q and Q′ are as defined previously. Of course the aminosilane or siloxane must contain an average of at least one silicon-bonded, amine-substituted hydrocarbon radical per molecule. The siloxanes can contain siloxane units without amino-substituted hydrocarbon radicals such as R′$_c$SiO$_{(4-c)/2}$ , as exemplified by MeSiO$_{3/2}$, PhSiO$_{3/2}$, PhMeSiO$_{2/2}$, Me$_2$SiO$_{2/2}$, Me$_3$ SiO$_{1/2}$, Me$_2$(OMe)SiO$_{1/2}$, ViMe$_2$SiO$_{1/2}$, and SiO$_{4/2}$ units where Me, Ph and Vi denote methyl, phenyl and vinyl, respectively, in addition to siloxane units that contain the required amino-substituted hydrocarbon radicals.

Preferred aminosilanes to be acylated have the formulae R′$_e$Si(QNHCH$_2$ CH$_2$ NH$_2$)$_{4-e}$ or R′ Si(QNH$_2$)$_{4-e}$ where "e" denotes a number having a value of 0, 1, 2, or 3. For example, the aminosilane can be Me$_3$SiCH$_2$ CH(CH$_3$)CH$_2$NHCH$_2$ CH$_2$ NH$_2$, (MeO)$_2$MeSiCH$_2$CH$_2$ CH$_2$ NH$_2$, (MeO)$_3$SiCH$_2$CH(CH$_3$)CH$_2$ NHCH$_2$ CH$_2$ NH$_2$, (MeO)$_3$SiCH$_2$ CH$_2$ CH$_2$ NH$_2$ or (MeO)$_2$MeSiCH$_2$ CH(CH$_3$)CH$_2$ NHCH$_2$ CH$_2$ NH$_2$.

Preferred aminosiloxanes to be acylated have the formula YR′$_2$ SiO(R$_2$ SiO)$_x$ (YR′SiO)$_y$ SiR′$_2$Y where each Y denotes, independently, an R′, —QNHCH$_2$ CH$_2$ NH$_2$ radical, at least one Y being an amino-substituted radical, and "x" and "y" denote numbers having average values of from 0 to 5000 and 0 to 500, respectively. Examples of preferred aminosiloxanes to be acylated by the method of this invention include, but are not limited to,

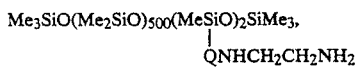

Me$_3$SiO(Me$_2$SiO)$_{500}$(MeSiO)$_2$SiMe$_3$,
|
QNHCH$_2$CH$_2$NH$_2$

H$_2$NCH$_2$CH$_2$NHQMe$_2$SiOSiMe$_2$QNHCH$_2$CH$_2$NH$_2$,

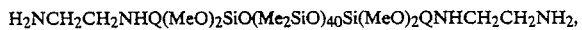

H$_2$NCH$_2$CH$_2$NHQ(MeO)$_2$SiO(Me$_2$SiO)$_{40}$Si(MeO)$_2$QNHCH$_2$CH$_2$NH$_2$,

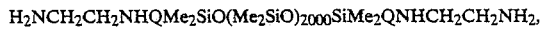

H$_2$NCH$_2$CH$_2$NHQMe$_2$SiO(Me$_2$SiO)$_{2000}$SiMe$_2$QNHCH$_2$CH$_2$NH$_2$,

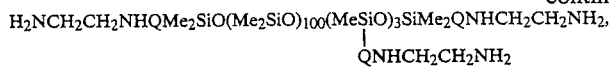

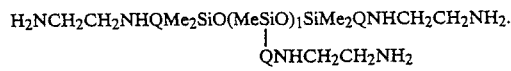

Aminosiloxanes can also have a cyclic or branched structure such as (YMe$_2$SiO)$_4$Si and (YMeSiO)$_4$, in addition to the linear structures noted above, wherein at least one Y denotes an amino-substituted radical.

Aminosilicon compounds and their preparation are well known in the organosilicon art. Some are commercially available. The disclosures of U.S. Pat. Nos. 2,557,803, 2,738,357, 2,754,312, 2,762,823, 2,998,406, 3,045,036, 3,087,909, 3,355,424, 3,560,543, 3,890,269, 4,036,868, 4,152,346, and 4,507,455 are incorporated herein by reference to further teach how to prepare aminosilicon compounds that can be used in the method of this invention.

The acyl halide is admixed to the aminosilicon compound in the presence of a metal alkoxide dissolved in a small amount of cosolvent. Preferably the cosolvent is methanol. The metal alkoxide is preferably an alkali metal alkoxide such as sodium methoxide.

While it is possible to conduct the instant reaction without use of a cosolvent, use of a cosolvent is greatly preferred. Because sodium methoxide is essentially insoluble in a solvent such as toluene, it is believed to be difficult for the undissolved sodium methoxide to adequately neutralize the amine hydrochloride which is formed as a part of the process. Unless the amine hydrochloride that is formed during the reaction is neutralized and the amine freed, further reaction with the acyl halide cannot take place. Use of a cosolvent system in which the bases are soluble to some extent overcomes this apparent problem.

Preferably a catalytic amount of cosolvent is used, i.e., an amount sufficient to effect transfer of the alkali metal alkoxide into the nonaqueous solvent. Thus for a mixture sodium methoxide and methanol cosolvent, the preferred range of methanol is about 1 to 25 wt. %. While it is possible to use larger amounts of methanol, limiting the presence of the cosolvent to such small amounts is greatly preferred. Thus, it has been found that when a relatively large amount of methanol cosolvent is used, such as that found in a 25 wt.% solution of sodium methoxide in methanol, long term stability may be impaired. This is believed to be due to the fact that in order to obtain an acrylamidoalkyl polysiloxane with a long term stable viscosity, it is desirable to convert a high percentage (>95%) of amine to amide. When a large amount of methanol cosolvent is used, the best conversion of amine to amide that could be achieved was found to be around 90-93%. This was apparently due to the occurrence of competing reactions, such as formation of methyl acrylate, which are facilitated in the presence of an excess of cosolvent. Thus in order to maximize amide formation and to minimize side reactions, it is desirable to reduce the concentrations of methanol to only a catalytic quantity when compared to sodium methoxide.

For example, when one half the weight of methanol compared to the weight of solid sodium methoxide is used, the conversion of amine to amide was found to be >95% and the resulting product exhibited a stable viscosity for at least 3 months.

In addition to the small amount of cosolvent for dissolving the metal alkoxide, a nonaqueous solvent is also used for the aminosilicon when the acyl halide is admixed to it. That solvent can be any suitable nonaqueous liquid that will not react with the components of the reaction. Preferably the solvent is also a solvent for the organosilicon product of the reaction.

Examples of suitable solvents include, but are not limited to, hydrocarbons such as toluene, xylene, hexane, cyclohexane and heptane; halogenated hydrocarbons such as methylene chloride, chloroform, trichloroethylene and trichloroethane; and oxygenated compounds such as ethyl ether and ethyl acetate. Mixtures of two or more solvents can also be used, it only being required that the mixture, and not necessarily all of the components in the mixture, be a solvent for the aminosilicon compound. Preferably solvents such as toluene or hexane are used. The amount of solvent that is used should be sufficient to dissolve the aminosilicon compound and, preferably, the organosilicon product as well.

The preferred components of the reaction mixture, i.e., the acyl halide, the aminosilicon compound, solvent, metal alkoxide and cosolvent, can be mixed in any manner as long as the acyl halide is added to the aminosilicon compound in the presence of the solvent, metal alkoxide and its cosolvent. In a preferred embodiment, the acyl halide or a solution thereof is added to a well agitated mixture of a solvent solution of the aminosilicon material and a cosolvent solution of the metal alkoxide.

Since acyl chloride reacts with methanol or sodium methoxide to form esters, about 10% excess acyl chloride, preferably acrylyl chloride, based on the amine content is preferably used for the reaction. A deficiency of acyl halide relative to the total number of reactive amino groups, although merely leading to the preparation of incompletely acylated product when the acyl halide is free of aliphatic unsaturation, leads to products which can undergo a Michael-Addition type reaction when the acyl halide contains aliphatic unsaturation. For this reason, it is preferred, although not required, to fully acrylate the aminosilicon compound when an acrylyl halide is used. An equimolar amount of sodium methoxide and acyl chloride are also preferably used so that the solution at the end of the reaction is neutral. A deficiency of sodium methoxide relative to the amount of hydrogen halide produced is to be avoided since an excess of hydrogen halide will inhibit the reaction from going to completion. Except when the acyl halide is an acrylyl halide, the method of this invention can be practiced at any reasonable temperature. Advantageously this method proceeds readily at room temperature.

When an acrylyl halide is used, this method should be practiced at a relatively low temperature to minimize the formation of byproducts. Accordingly, when using the method of this invention to prepare acrylyl-substituted aminosilicon compounds, the reaction should be conducted at a temperature of from −10° C. to +10° C. Lower reaction temperatures are suitable particularly since no aqueous phase is present, but higher reaction temperatures will substantially reduce the yield of desire product.

During and after the addition of the acyl halide component to the aminosilicon component, the reaction mixture should be thoroughly agitated to maintain an intimate contact between the metal alkoxide and the hydrogen chloride. The usual low shear means such as stirrers, paddles, and impellers are sufficient to maintain sufficient agitation. Agitation is maintained until the acylation reaction is finished, typically within an hour. After the reaction is finished, the product of the reaction can be separated from the solvent or allowed to remain in the solvent as desired. When acrylyl-substituted products are to be separated from the solvent, it is desirable to add a polymerization inhibitor such as sodium nitrite to the solution prior to any separating action such as distilling or fractionation.

The products of this method are useful as polar silicon-containing additives for cosmetic compositions, coating compositions, textile treating compositions, and paints. The compositions are useful as comonomers with polymerizable vinyl monomers such as styrene, butadiene, methyl methacrylate, ethyl acrylate, vinyl acetate, vinyl chloride, vinylidene chloride and acrylonitrile. In particular the compounds having acrylylamine-substituted hydrocarbon radicals are useful as a reactive component in free radical curable compositions such as radiation curable coupling agents, as adhesion promoters, and as a component of dual cure systems.

The following examples are disclosed to further teach the practice of the invention and are not intended to limit the invention as it is delineated in the claims.

EXAMPLE 1

1-Methyl-1,1-bis(trimethylsilyloxy)-1- {3-N-(2-aminoethyl)-3-aminoisobutyl}silane was reacted with acrylyl chloride in toluene in the presence of a 25 wt % solution of sodium methoxide in methanol. One and one tenth equivalents of acrylyl chloride and 1.1 equivalents of sodium methoxide based on the amine neutral equivalent (ANE) of the starting amine was used (10% excess). The sample was washed with a saturated sodium chloride solution. Conversion of amine to amide in the washed sample was determined to be 92–93%. Infrared analysis and proton NMR analysis were used to confirm the structure of the resulting product.

EXAMPLE 2

A one liter, three-necked flask equipped with a thermometer, stirring paddle, air tight stirring sleeve, $N_2$ inlet and dropping funnel was charged with aminopropyltrimethoxysilane (100.0 g, 0.558 moles), toluene (160.1 g), sodium methoxide (33.16 g, 0.614 moles) and methanol (10.11 g). The mixture was stirred under N, atmosphere and cooled to 0° C using a dry ice/isopropanol bath. To this, 55.37 g (0.614 moles) of acrylyl chloride dissolved in 100 g of toluene was added gradually over a period of 30 minutes. The mixture was agitated for another 30 minutes. By-product sodium chloride was removed by filtration and the solvent was removed under reduced pressure to obtain acrylamidopropyltrimethoxysilane in essentially quantitative yield. Sodium nitrite (0.001 g) was added as an inhibitor.

EXAMPLE 3

A 500 ml three-necked flask equipped with a thermometer, mechanical stirrer, and dropping funnel with a $N_2$ inlet was charged with 50 g of

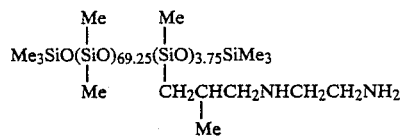

(amine neutral equivalent 703; 71.12 mmole of amine) dissolved in 100 ml of toluene. Sodium methoxide (4.22 g, 78.1 mmole) and 2.5 ml of methanol was added to the solution. The reaction mixture was stirred and cooled to 0° C. Acrylyl chloride (7.06 g, 78.1 mmole), dissolved in 20 ml of toluene was gradually added to the stirred reaction mixture, maintaining the temperature at 0° C. After the addition of acrylyl chloride was complete, the mixture was stirred for an additional half hour. Since the solution was slightly acid (6.5 by pH paper), 0.7 g of potassium carbonate was added and the mixture stirred for another 30 minutes. The salts were removed by filtration and the solvent removed under reduced pressure. The conversion of amine to amide was found to be quantitative since the residual amine content in the product was negligible as determined by perchloric acid titration.

EXAMPLE 4

In a 500 ml three necked flask equipped with a thermometer, a mechanical stirrer, a dropping funnel and a $N_2$ inlet tube was placed 25 g of amine functional phenylhydrolyzate resin (amine neutralization equivalent 720) dissolved in 100 ml of dry toluene. Dry methoxide (2.06 g) dissolved in 2 ml of dry methanol was added. The reaction flask was cooled in an ice bath. Acrylyl chloride (3.45 g) dissolved in 5 ml of toluene was added while stirring the ingredients in the flask, at a rate to maintain the reaction temperature below 5° C. After the addition was over, the contents were allowed to warm to room temperature. The salts were removed by filtration and the solvents removed under reduced pressure to obtain the product in more than 95% yield.

EXAMPLE 5

Using the procedure outlined in Example 4, 20 g of amine functional hydrolyzate obtained from the cohydrolysis of $PhSiCl_3$ and $n-propylSiCl_3$ (70′ 30 wt/wt, respectively) was dissolved in 80 ml of toluene and reacted with 1.72 g of NaOMe in 2 ml of methanol to obtain the corresponding acrylamide functional resin in 95% yield.

That which is claimed is:

1. A method for preparing an organosilicon compound containing at least one silicon-bonded acylamino-substituted hydrocarbon radical comprising: reacting an acyl halide with an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent, silicon-linking, oxygen atoms, in the presence of a non-aqueous solvent, a metal alkoxide, and a non-aqueous cosolvent for said metal alkoxide.

2. The method according to claim 1 wherein said silicon-bonded amino-substituted hydrocarbon radical has the formula $-Q(NHQ')_a NZH$ and the acyl halide has the formula $R''COX$, wherein Q and Q' denote divalent hydrocarbon radicals, R'' denotes a substituted or unsubstituted monovalent hydrocarbon radical, X denotes a halogen atom, denotes a hydrogen or a monovalent hydrocarbon radical, and "a" has a value of 0 or 1.

3. A method according to claim 2 wherein said acyl halide is a compound selected from the group consisting of acrylyl chloride, methacrylyl chloride, and cinnamoyl chloride.

4. A method according to claim 3 wherein said aminosilicon compound has the average unit formula $R'_c (NH_2 (Q'NH)_a Q)_d SiO_{(4-c-d)/2}$ wherein R' denotes a radical selected from the group of radicals consisting of monovalent hydrocarbon radicals and alkoxy radicals, "c" has a value of from 0 to 3, "d" has a value of >0 to 4, and "c"+"d" has a value of 1 to 4.

5. A method according to claim 4 wherein silicon atoms without said amino-substituted hydrocarbon radicals have the formula $R'_c SiO_{(4-c)/2}$.

6. A method according to claim 4 wherein said aminosilicon compound is a siloxane having the formula $YR'_2SiO(R_2SiO)_x (YR'SiO)_y SiR'_2Y$ wherein Y denotes R' or $-QNHCH_2CH_2NH_2$, "x" has a value of from 0 to 5000, and "y" has a value of from 0 to 500.

7. A method according to claim 4 wherein said aminosilicon compound is a silane having the formula $R'_e Si(QNHCH_2 CH_2NH_2)_{4-e}$ wherein e has a value of 0, 1, 2, or 3.

8. A method according to claim 4 wherein R' is selected from the group consisting of methyl, phenyl, vinyl, and methoxy.

9. A method according to claim 1 wherein said acyl halide is admixed to a mixture of said aminosilicon compound, nonaqueous solvent, alkaline material, and nonaqueous cosolvent.

10. A method according to claim 9 wherein the resulting mixture obtained by admixing said acyl halide is thereafter agitated until said organosilicon compound is formed.

11. A method according to claim 1 further comprising isolating said organosilicon compound.

12. A method according to claim 1 wherein said reaction is carried out at a temperature of from about $-10$ to $+10°$ C.

13. A method according to claim 1 wherein said metal alkoxide is an alkali metal alkoxide.

14. A method according to claim 13 wherein said alkali metal alkoxide is sodium methoxide.

15. A method according to claim 1 wherein said nonaqueous solvent is selected from the group consisting of toluene and hexane.

16. A method according to claim 1 wherein said cosolvent is methanol.

17. A method according to claim 1 wherein the molar amounts of said metal alkoxide and said acyl halide are about equal.

18. A method according to claim 1 wherein the molar amount of said acyl halide is in about 10% molar excess over the molar amount of said nitrogen-bonded hydrogen atoms of said aminosilicon compound.

19. A method according to claim 14 wherein said cosolvent is methanol.

20. A method according to claim 19 wherein the weight percent of said methanol in a mixture of said methanol and said sodium methoxide is about 1 to 25 weight percent.

* * * * *